United States Patent [19]

Abrevaya

[11] Patent Number: 4,945,116

[45] Date of Patent: Jul. 31, 1990

[54] FISCHER-TROPSCH SYNTHESIS PROCESS EMPLOYING A MODERATED RUTHENIUM CATALYST

[75] Inventor: Hayim Abrevaya, Wilmette, Ill.

[73] Assignee: UOP, Des Plaines, Ill.

[21] Appl. No.: 290,398

[22] Filed: Dec. 29, 1988

[51] Int. Cl.$^5$ .............................................. C07C 1/04
[52] U.S. Cl. .................................................... 518/715
[58] Field of Search ........................................ 518/715

[56] References Cited

U.S. PATENT DOCUMENTS

| | | | |
|---|---|---|---|
| 4,415,676 | 11/1983 | Tsang et al. | 518/715 |
| 4,714,692 | 12/1987 | Abrevaya et al. | 502/261 |
| 4,714,693 | 12/1987 | Targos | 502/261 |
| 4,738,948 | 4/1988 | Iglesia et al. | 502/326 |

FOREIGN PATENT DOCUMENTS

WO85/4598  10/1985  PCT Int'l Appl. .

OTHER PUBLICATIONS

Okuhara et al., J. of Catalysis 95, 41–48 (1985).
Abrevaya, H. et al., "Metal Particle Size Effects in Fischer-Tropsch Synthesis with Supported Ruthenium Catalysts", during mtg. of Catalysis Society and reprinted in Catalysis 1987 ed. by J. W. Ward, copyright 1988.
Lin, Zhneg-Zhong et al., "Morphology of Ru Particles on $Al_2O_3$ and its Effect on Selectivity in Catalytic Hydrogenation of Carbon Monoxide", pp. 913–914, Chemistry Letters of the Chemical Society of Japan for 1986.
Lin, Zheng-Zhong et al., "Pronounced Effect of Particle Size on Selectivity Observed for Carbon Monoxide Hydrogenation Over Ruthenium-Alumina Catalyst", J. Chem. Soc., Chem., Commun., 1986, at p. 1673.
Okaraha, Toshio et al., "Effects of Additives on the Selectivity in Fischer-Tropsch Synthesis by Alumina-Supported Ruthenium Catalyst", published in Chemistry Letters (9), 1491-4, 1984.

Primary Examiner—Howard T. Mars
Attorney, Agent, or Firm—Thomas K. McBride; John F. Spears, Jr.

[57] ABSTRACT

A Fischer-Tropsch type process produces hydrocarbons from carbon monoxide and hydrogen using a novel catalyst comprising moderated ruthenium on an inorganic oxide support. The preferred moderator is silicon. Preferably the moderator is effectively positioned in relationship to ruthenium particles through simultaneous placement on the support using reverse micelle impregnation.

14 Claims, 1 Drawing Sheet

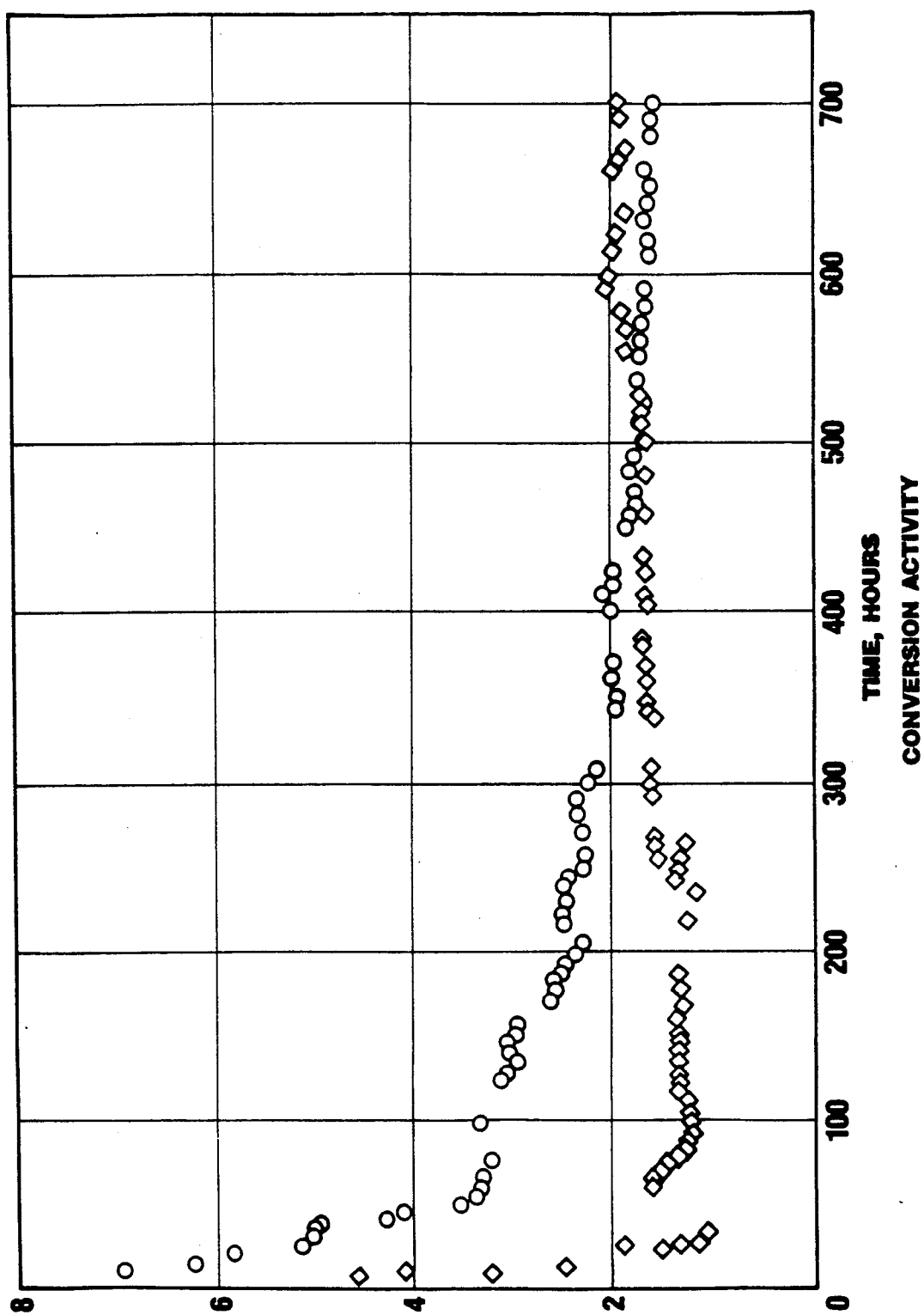

FISCHER-TROPSCH SYNTHESIS PROCESS EMPLOYING A MODERATED RUTHENIUM CATALYST

The Government of the United States of America has rights in this invention pursuant to Contract No. DE-AC22-84PC70023 awarded by the U.S. Department of Energy.

BACKGROUND OF THE INVENTION

The invention relates to the production of hydrocarbons from carbon oxides and hydrogen or a hydrogen source, commonly referred to as the Fischer-Tropsch process. The invention specifically relates to a novel catalyst comprising moderated ruthenium on an inorganic oxide support. The invention specifically relates to a Fischer-Tropsch process employing a catalyst comprising uniformly sized particles of ruthenium in effective contact with silicon, which functions to moderate the electronic characteristics of the ruthenium.

PRIOR ART

The Fischer-Tropsch process has utility as a process for producing synthetic motor fuels from carbon sources available as carbon oxides, specifically carbon monoxide. One source of the carbon monoxide is a solid fossil fuel such as coal.

The wide availability and surplusage of low cost and low value methane coupled with the relatively high value of multicarbon atom compounds has also generated continued interest in the conversion of methane to hydrocarbons of higher carbon number. That is, it is economically desirable to be able to convert methane to higher carbon number hydrocarbons. This has also led to continuing research in the area of Fischer-Tropsch synthesis. One proposed route is the conversion of methane to carbon monoxide and hydrogen. This raw synthesis gas is then used as the feed to the Fischer-Tropsch unit.

Many of the Fischer-Tropsch catalysts which have been proposed are based upon the use of ruthenium supported upon an inorganic oxide. For instance, U.S. Pat. No. 4,738,948 issued to E. Iglesia et al. describes a catalyst comprising cobalt and ruthenium supported on titania. This reference is believed pertinent for its teaching in regard to the use of titania for Fischer-Tropsch catalyst, its description of the overall Fischer-Tropsch process, products and conversion promoting-conditions.

Significant work has been done to characterize the effect of the ruthenium particle size on Fischer-Tropsch catalyst. For instance, such work is described in the article entitled, "Metal Particle Size Effects in Fischer Tropsch Synthesis with Supported Ruthenium Catalysts" authored by H. Abrevaya et al. given during the proceedings of the 10th North American meeting of the Catalysis Society, San Diego, Calif., May 17–22, 1987 and reprinted in *Catalysis* 1987 edited by J. W. Ward and published by Elsevier. This paper is pertinent for its description of the preparation, physical characteristics and performance of several catalysts comprising ruthenium supported on alumina, with the catalysts differing in the size of the ruthenium particles. The reference is also pertinent in that the catalysts were prepared using the reverse micelle technique preferred for use in the preparation of the subject catalyst. The paper reported that particles larger than 4 nanometers were stable on alumina whereas smaller particles would tend to agglomerate.

The effect of ruthenium particle size on the performance of Fischer Tropsch catalyst is also described in an article appearing at pages 913–914 of the Chemistry Letters of the Chemical Society of Japan for 1986 in a paper entitled, "Morphology of Ruthenium Particles on Alumina and Its Effect on Selectivity in Catalytic Hydrogenation of Carbon Monoxide", with a principal author of Zheng-Zhong Lin. This reference is pertinent for its teaching of the use of ruthenium supported on alumina for Fischer Tropsch processing together with its description of the effect of ruthenium particle size on the products and turnover rate in the desired reaction. Further description of the effect of particle size on product distribution is given in another article by Zheng-Zhong Lin et al., entitled, "Pronounced Effect of Particle Size on Selectivity Observed for Carbon Monoxide Hydrogenation Over Ruthenium-Alumina Catalyst". Small particles (10 Angstroms) are described as giving significant proportions of higher hydrocarbons while large single crystallites (110 Angstroms) gave mainly methane. This article was published in the *J. Chem. Soc.*, "Chem. Commun.", 1986 at page 1673.

In a paper by Toshio Okaraha et al. entitled, "Effects of Additives on the Selectivity in Fischer-Tropsch Synthesis by Alumina-Supported Ruthenium Catalyst" published in *Chemistry Letters*, (9), 1491–4, 1984, there is described the addition of potassium and phosphorus to ruthenium on gamma alumina catalyst for Fischer-Tropsch processing. The article describes the changes in the selectivity of the catalyst as being effected mainly by the altered electronic state of the ruthenium. This reference is believed pertinent for its teaching that those skilled in the art have considered the effects of added elements upon the electronic state of the ruthenium atoms or particles used in this catalyst. It is also believed pertinent for its showing that those skilled in the art are capable of assessing such changes in electronic states of catalyst metal elements. This reference also refers to the addition of alkali metals, vanadium or manganese to the catalyst.

PCT application WO85/4598 describes Fischer-Tropsch catalysts for the production of $C_5$ plus hydrocarbons, which catalysts are prepared by mixing an active metal precursor, which may be ruthenium, and a promoter such as alkali metal with a hydrolyzable compound of a number of elements including silica and alumina followed by hydrolysis to form a porous amorphous framework matrix containing uniformly distributed active metals and promoters. One exemplified catalyst comprises ruthenium, iron and potassium supported on a silica-alumina. Although silicon is apparently described as being present during the production of the catalyst, it is not believed to be employed as a moderator to the ruthenium metal but rather is employed as a support component. Thus there is no apparent teaching in the reference suggesting the subject composition or process.

U.S. Pat. No. 4,714,693 to W. M. Targos is pertinent for its teaching of a preferred method for making a catalyst for use in the subject invention. This patent discloses the reverse micelle impregnation technique, which preferably is utilized to ensure proper metal particle size. Use of this method should provide placement of the moderator element in close and effective proximity to the active ruthenium component of the catalyst as noted below. It must be noted that this reference indicates the reverse micelle technique could be used to place more than one element on the inorganic oxide support at the same time. The reference specifically names a number of metals and broadly lists Groups I-A, II-A, III-B, IV-B, V-B, VI-B, VII-B, I-B, II-B, III-A, IV-A, V-A, and the lanthanum series metals. However, this reference apparently does not suggest the use of silicon as a moderator for the ruthenium in Fischer-Tropsch catalyst. Specifically mentioned metals include gallium, indium, germanium, tin, antimony, and potassium.

U.S. Pat. No. 4,738,948 issued to E. Iglesia et al. is believed pertinent for presentation of a Fischer-Tropsch synthesis catalyst comprising cobalt and ruthenium in intimate contact. It is also believed pertinent because sophisticated analytical techniques such as high resolution transmission electron microscope with scanning transmission and energy dispersive X-ray analysis were used to characterize the metals on the catalyst. The cobalt and ruthenium may be co-impregnated, with calcination of the catalysts yielding improved performance.

BRIEF SUMMARY OF THE INVENTION

The invention comprises a novel catalyst for use in the Fischer-Tropsch hydrocarbon synthesis reaction and a process employing the novel catalyst. The novel catalyst comprises an inorganic oxide support, preferably alumina, having dispersed thereon particles of ruthenium which are mainly of a particle size between 40 and 60 Angstroms plus a modifier component in effective relationship with the ruthenium particles to cause an electronic modification of the ruthenium atoms' outer electrons. Preferably, the modifier component is silicon. It has been determined that this catalyst composition provides a somewhat moderated initial Fischer-Tropsch synthesis conversion activity but that the catalyst has exceedingly high stability and good selectivity.

One embodiment of the invention may accordingly be characterized as a process for producing $C_3$-plus hydrocarbons from carbon oxides which comprises contacting a feed stream comprising hydrogen and carbon monoxide with a solid catalyst in a reaction zone maintained at conversion-promoting conditions and producing an effluent stream comprising $C_{3-plus\ hydrocarbons}$, with the catalyst comprising (i) an inorganic oxide support; (ii) about 0.3–6.0 wt. percent ruthenium present as particles of about 40–60 Angstroms and (iii) about 0.1–5 wt. % of a modifier component chosen from the group consisting of boron, aluminum, gallium, indium, silicon, germanium, tin, lead, arsenic, antimony and bismuth.

BRIEF DESCRIPTION OF THE DRAWING

The Drawing presents a graph of the conversion activity versus time of an unmodified prior art ruthenium catalyst (circles) and that of a catalyst of the subject invention comprising silicon modified ruthenium.

DETAILED DESCRIPTION

Fischer-Tropsch synthesis reactions can be employed in the production of synthetic fuels directly from available carbon oxides and hydrogen. However, the process is primarily investigated for the production of synthetic liquid fuels to alleviate shortages or to ensure an adequate supply when convention sources of hydrocarbons are scarce. Significant research is conducted in this area with the hope of providing a means of indirectly converting a portion of the large quantities of coal, peat, and other heavy hydrocarbonaceous materials into high quality liquid fuels for transportation purposes such as gasoline and diesel fuel.

It is an objective of the subject invention to provide an improved process and an improved catalyst for performing the Fischer-Tropsch synthesis reaction. A large amount of effort has been directed to the development of low-cost iron-based catalysts Because of the high cost of ruthenium, a ruthenium-based catalyst must be more active and stable than an iron-based catalyst. It is a specific objective of the subject invention to provide a ruthenium based Fischer-Tropsch catalyst having improved stability.

The catalyst of the subject invention comprises three basic components. The first fundamental component is the support material which carries the active catalytic components. The support material is preferably a refractory inorganic oxide. It is believed that suitable catalysts can be prepared utilizing a number of inorganic oxides including silica, silica-alumina, titania, magnesia and other known oxide materials. The support or carrier material would normally be formed into small particles such as spheres, extrudates, pellets, cubes, etc. including multilobial extrudates. Alternatively, the support material may be extruded or in other ways formed into a honeycomb-type monolith similar to that widely employed in automotive catalytic converters used to reduce the concentration of hydrocarbons and nitrous oxides in automotive exhaust gas. The preferred support material is alumina, with gamma alumina being especially preferred.

The second major component of the subject catalyst is a ruthenium component. Preferably, the ruthenium component is present on the support material as essentially elemental ruthenium, although portions of the ruthenium may be present in the form of an oxide or in the form of a compound with the modifier component described below. The catalyst must contain a catalytically effective amount of the ruthenium component. A broad range of ruthenium contents extends from 0.3 to 8 wt. percent. It is preferred that the ruthenium content of a catalyst is between 0.3 to 6 wt. percent. It is highly preferred that the ruthenium content is between 1.0 and 4 percent.

In order to achieve the desired performance of the catalyst the great majority of the ruthenium should be present in a relatively narrow particle size falling between 40 and 60 Angstroms. It is therefore preferred that over 75 wt. percent of the ruthenium present on the catalyst is present as crystallites having a size distribution ranging from about 40 to 60 Angstroms. More preferably at least 80 wt. percent of the ruthenium is present as crystallites falling within this size range.

It is also important to the subject invention that the ruthenium is an electron deficient state, relative to unmodified ruthenium, as measured by ESCA (Electron Spectroscopy for Chemical Analysis) monitoring of the $3p_3$ electron binding energy. The amount of shift in the binding energy of this electron should be at least 0.1 positive electron volts. A preferred range of shift in this binding area is from 0.1 to 0.25 electron volts.

Excessive electron deficiency causes poorer catalyst performance. For example, a catalyst was prepared using reverse micelle techniques as described below but using iridium as the modifier component of a ruthenium on alumina catalyst. The binding energy shift of this catalyst was approximately 0.38 electron volts. The iridium-modified catalyst was essentially inactive at the same test conditions. Hence, iridium is believed to be inappropriate as a modifier component.

While not wishing to be bound to any theory explaining the subject invention, it is believed that the modifier may reduce the electron density of the active catalyst metal, possibly resulting in a weakening of the bond between carbon and the active metal. Carbon which is not strongly bound to the surface can be hydrogenated easily, resulting in minimal carbon accumulation. Weakening the metal-carbon bond strength would also possibly lower the CO dissociation rate. This would minimize coking reactions since coking results when the dissociative adsorption rate of CO exceeds the removal rate of carbon, i.e. by hydrogenation.

Examination of a silicon-modified ruthenium catalyst by X-ray photoelectron spectroscopy (XPS) showed some minor reduction in p-electron density of the ruthenium relative to the ruthenium in the catalyst without the modifier. This XPS result, along with attenuation of ruthenium's initial activity and improvement of its stability by silicon, are consistent with the expected role of the modifier discussed here.

Alternatively, the modifier atoms may locate themselves between active metal atoms, resulting in a reduction in the number of adjacent active metal atoms. Since CO dissociation requires several adjacent vacant metal atoms, the dilution effect of the modifier may decrease the CO dissociation rate, and, therefore suppress coking reactions, as explained above.

Whether the modifier has a chemical or geometrical effect, an attenuation of initial activity is therefore expected when CO dissociation is the rate determining step.

The third major component in the catalyst is a modifier component. It is contemplated that a number of different elements will perform as effective modifier components. Specifically, it is contemplated that the modifier could be one or more metals chosen from the group consisting of aluminum, boron, indium, silicon, germanium, tin, lead, arsenic, antimony, and bismuth. These materials fall within Groups III-A, IV-A, and V-A of the Periodic Table of the Elements in the form widely used in the United States as exemplified by the Table provided in the inside front cover of the fourth edition of the *Chemical Engineer's Handbook* as edited by J. H. Perry, McGraw-Hill, 1963.

The most highly preferred modifier component is silicon. There is, however, no apparent reason why the composition of the subject catalyst is confined to the use of this single modifier element. Therefore, it is contemplated that combination of two or more of the above-mentioned modifier elements may be utilized as the modifier component of the subject catalyst For instance, the modifier component could comprise silicon and indium, silicon and tin, or silicon and bismuth. Alternatively, the modifier component could comprise other combinations such as indium and tin, antimony and bismuth, or antimony and indium. The modifier should be present in a concentration in the finished catalyst ranging between 0.1 to 7.8 wt. percent. Preferably the modifier component is present in a concentration ranging from 0.1 to 5 wt. percent. A modifier concentration in the range of from 1 to 4.5 wt. percent is highly preferred. These concentrations refer only to the material present in the catalyst as modifier to the ruthenium. They therefore exclude, for instance, silicon present in silica or silica-alumina which may be present in the catalyst as a support or part of the support or as an extrusion aid, etc.

To the best of present knowledge, it is not necessary to concentrate the modifier component in any particular location upon the surface of the support material. The modifier component must however be in active placement close enough to the ruthenium particles to affect the desired shift in the electron state of the ruthenium electrons. The modifier component may be uniformly spread across the surface of the support material through the use of conventional ion exchange or impregnation type techniques. However, it is highly preferred that the modifier component is placed upon the support material during a simultaneous reverse micelle impregnation step. As used herein the term "simultaneous reverse micelle impregnation" is intended to indicate that both the ruthenium component and the modifier component are present within the same micelle of the reverse micelle solution used to impregnate the ruthenium component upon the support material.

The preferred technique for applying the ruthenium and the modifier component to the support material is the reverse micelle technique described and exemplified in U.S. Pat. No. 4,714,692 to H. Abrevaya et al. and in U.S. Pat. No. 4,714,693 to W. M. Targos. Both of these patents are incorporated herein in their entirety. Basically, this impregnation technique comprises contacting the support with water cores containing ions of the metals which it is desired to deposit upon the support material. The metals are contained in a microemulsion which is a thermodynamically stable solution of water, hydrocarbons, and at least one surfactant.

In a reverse micelle system, the water core is surrounded by the polar head groups of the surfactant. The nonpolar portion of the surfactant extends into the nonpolar hydrocarbon solvent solution thus forming the reverse micelle. When metals are dissolved in the water used in the preparation of the reverse micelle, the metals become encapsulated in the water core. The individual water cores which make up the reverse micelle solution are isolated from one another by the nonaqueous environment. An important factor which contributes to the size of the metal particle formed on the catalyst is the amount of water present in each individual microemulsion. Very small amounts of water are preferred in the present invention. Even though amounts as high as 5 wt. percent may be employed, it is preferred to employ less than 4 wt. percent, and more preferably less than 3 wt. percent. Preferably, the size of the water core is in the range of about 10 to 200 Angstroms and more preferably in size range of about 20 to 90 Angstroms.

The surfactant employed in the reverse micelle impregnation technique will possess both polar and nonpolar characteristics. The surfactant may be nonionic, ionic or cationic. Polyethylene dodecyl glycol ethers are preferred nonionic surfactant compounds. Nonionic surfactants comprising about 10 to 16 carbon atoms in the carbon chain are preferred. Suitable anionic surfactant compounds include sodium dodecyl sulfate. Suitable cationic surfactant compounds include cetyl trimethyl ammonium halides. A particularly preferred cationic surfactant is cetyl trimethyl ammonium bromide. Suitable cosurfactants include medium chain length alcohols such as N-octanol.

The surfactant may be present in the solution a concentration range of 5 to 40 wt. percent. Preferably the surfactant is present in a concentration range of 15 to 28 wt. percent. The weight ratio range of surfactant to water is preferably from about 6:1 to 24:1.

A cosurfactant, such as a medium chain length alcohol, can be added to the oil plus water plus surfactant mixture to lower the interfacial tension between the insoluble phases and therefore allow a further decrease in micelle size. Suitable cosurfactants include straight chain aliphatic alcohols. Preferably, the alcohols have from 3 to 6 carbon atoms per molecule. Propanol, butanol, pentanol, and hexanol are preferred.

The selection of a proper metal compound is important in the production of high quality oatalysts. In order to be effective as the impregnant medium, a high metal concentration in the water core is necessary. If the metals content is too low, the resulting aggregate amount of metal deposited on a support carrier will be too small to provide the desired catalytic activity. More importantly, the particle size distribution will fall below the size range specified above as preferred for the subject invention. Therefore, the use of compounds having a high metal solubility is contemplated. The metal ion concentration in the water core of the reverse micelles is preferably greater than 0.1 mole per liter. More preferably, the metal ion concentration in the water core should be at least 0.5 mole per liter. Most preferably, the metal ion concentration in the water core is in the range of about 0.5 to 1.5 moles per liter. Metal compounds suitable for use in preparing the subject catalyst include the metal salts and acids. Thus the use of chloryl metal acids as well as metal chlorides is contemplated. It is particularly preferred that the ruthenium component is provided through the use of ruthenium nitrosyl chloride dissolved in the water. It is contemplated that the solubility of the metals may be increased through lowering the pH of the aqueous solution as by adding concentrated hydrochloric acid.

The reverse micelle impregnant solution may be prepared by first dissolving the metal compounds in water to form a metal ion solution. The metal ion solution is subsequently admixed with a previously prepared admixture of surfactant and hydrocarbon solvent. The admixture of the two solutions provides a clear solution containing the reverse micelles.

A preferred impregnation technique comprises contacting the support material with the impregnant solution with mixing or agitation being provided to assure good contact. A contacting time of 5 minutes is sufficient. The support material is then drained of the remaining impregnant solution and subjected to an air drying procedure to remove the residual organic compounds which remain on the support. A helium purge at from about 50 to 300° C. may then be employed to remove residual organics. Finally, an air oxidation at a temperature of 200 to 600° C. is performed. The metal containing micelles impregnated on the support are subjected to a reducing atmosphere while on the surface of the support by contact with flowing hydrogen at about 200 to 600° C. The metal compounds on the support are reduced while on the support surface by contact with the flowing hydrogen. This provides the desired distribution and adhesion of the metal. Further details on the preparation of catalyst using the preferred reverse micelle technique is provided in the references cited above.

The feed gases charged to the subject process must comprise hydrogen or a hydrogen source and carbon oxides. Preferably the hydrogen is provided by free hydrogen, although some Fischer-Tropsch catalysts have sufficient water gas shift activity to convert some water to hydrogen for use in the Fischer-Tropsch process. The preferred carbon oxide is carbon monoxide. As the intended products contain more atoms of hydrogen per molecule than of carbon, it is preferred that the mole ratio of hydrogen to carbon oxides in the feed gas is greater than 1:1. Preferably the feed gas stream contains hydrogen and carbon monoxide in a mole ratio greater than 2:. A preferred range of hydrogen:CO mole ratios is from about 1.0 to 2.5. The feed gas may additionally contain carbon dioxide. The feed gas should be clean and treated as necessary to prevent the passage of undesirable elements or compounds into the reaction zone. For instance, it is preferred that the feed gas stream have a low concentration of compounds or elements having a deleterious effect upon the catalyst. It may therefore be necessary to treat the feed gas stream to ensure low concentrations of sulfur or nitrogen compounds including hydrogen sulfide, ammonia and carbonyl sulfides.

The feed gas stream is contacted with the catalyst in a reaction zone. Mechanical arrangements of conventional design may be employed as the reaction zone. Preferably the gas flows downward through the catalyst or radially outward across a catalyst bed. The gas hourly space velocity through the reaction zone, based upon total fresh feed may range from about 15 to about 1500 with a preferred range being from 50 to 750. Reaction zone temperatures in the range of from about 170° C. to about 310° C. may be employed. Preferably the reaction zone is operated at conversion-promoting conditions including a temperature of from 190° C. to about 260° C. Conversion-promoting conditions are intended to include a pressure above 6 atmospheres absolute and preferably above 10 atmospheres absolute. Pressures in the range of from about 10 to about 70 atmospheres may be employed.

The products produced in the subject process will have a great range of molecular weights. Normally the carbon number range of the product hydrocarbons will extend upward from methane to the limits discernable by modern analysis on the order of 50 to 100 carbon atoms per molecule. One measure of the performance capabilities of a catalyst is the amount of methane produced. As it is an objective of the process to produce hydrocarbons boiling in the range of transportation fuels, the production of methane, and other light hydrocarbons is undesirable. Therefore, the catalyst should produce less than 3 percent methane after it is lined out. Preferably the rate of carbon atom selectivity for methane should be below 2 percent.

The wide range of hydrocarbon species produced in the reaction zone will normally result in some of the product hydrocarbons being present as liquid phase materials at the reaction zone operating conditions. Therefore, the effluent stream of the reaction zone will often be a mixed phase stream. The effluent stream of the reaction zone may be cooled to effect the condensation of additional amounts of hydrocarbons and passed into a vapor-liquid separation zone. The vapor phase material may be passed into a second stage of cooling for the recovery of additional hydrocarbons. The liquid phase material from the initial vapor-liquid separation zone together with any liquid produced in a subsequent separation zone may be fed into a fractionation column. Normally a stripping column is employed first to remove light hydrocarbons such as propane and butane. The remaining hydrocarbons may be passed into a fractionation column wherein they are separated by boiling point range into such products as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reaction zone effluent stream after hydrocarbon recovery may be partially recycled to the reaction zone if it contains a sufficient quantity of hydrogen and/or carbon monoxide.

EXAMPLES

A reference catalyst was produced using the preferred reverse micelle technique. The finished catalyst contained 2.8 wt. % ruthenium on gamma alumina and had a narrow size distribution of ruthenium particles in the 4-6 nm size range. There was no modifier component present on the catalyst. This catalyst was tested at an inlet temperature of 208° C. and a pressure of 62 atm with a $2H_2:1CO$ feed gas at a CO conversion level of about 75-85% in a fixed bed reactor for 700 hours. This catalyst was not stable and accordingly, the gas hourly space velocity was lowered from an initial value of 500 $hr^{-1}$ to 147 $hr^{-1}$ during the first 530 hours on stream, after which no further space velocity change was made. The inlet temperature was increased to 210° C. between 700 hours and 825 hours on stream. The CO conversion was about 72% at the end of the test.

A catalyst conforming to the subject invention was made using the micelle technique to prepare a silicon-modified ruthenium catalyst with the same ruthenium level as the ruthenium-only-catalyst. Both silicon and ruthenium were contained within the micelles. The silicon-modified catalyst, while it consisted mostly of 4-6 nm ruthenium particles, had also some 10-20% of the ruthenium in the 3-4 nm and 6-40 nm size range. The silicon-modified catalyst was tested under the same conditions as the ruthenium-only-catalyst.

The initial activity of the silicon-modified catalyst was lower. The catalyst showed deactivation during the first 20 hours from about 60% to about 30% CO conversion. The gas hourly space velocity was lowered from 500 hr to 125 hr−1 during the first 20 hours in order to achieve high conversion. The CO conversion increased close to 90%, followed by a decrease to 70% at about 100 hours. The activity of the silicon-modified ruthenium catalyst then gradually increased! It achieved a CO conversion level of about 85% at 375 hours on stream, after which the gas hourly space velocity was gradually increased to 150 $hr^{-1}$ by 595 hours to prevent the conversion from exceeding 85%. The catalyst temperature was increased by 2° C. after 700 hours on stream in order to compensate for some of the space velocity increase which was apparently done too rapidly.

The activities of the ruthenium catalysts with and without the silicon modifier as a function of time are compared in the Figure. The drawing shows the global reaction rates, moles $CO+H_2$ converted/hour-moles ruthenium, of the two catalysts during the first 700 hours of the tests. The conversion activity of the unmodified catalyst is indicated using circles and that of the subject catalyst is shown by the diamonds. The results indicate that silicon attenuated the ruthenium's initial activity by about 50%. The catalyst without the modifier deactivated with a rate which decreased with time on stream. The silicon-modified catalyst lost activity during the first 20 hours, after which it gradually gained activity.

After about 525 hours on stream the silicon-modified catalyst's activity was better relative to the catalyst without the modifier. As may be seen from the drawing the activity of the unmodified catalyst was decreasing during later portions of the time period shown. In contrast the activity of the subject catalyst was increasing at these conditions.

The methane selectivities of the two catalysts were compared. During the first 500 hours the methane selectivity with the silicon-modified catalyst was higher relative to the catalyst without the modifier. After 500 hours the two catalysts showed essentially the same methane selectivity, between 1.3% and 1.4%. The methane selectivity increased with both catalysts, after 700 hours on stream, caused by a 2° C. temperature increase in the catalyst bed. 0.4% higher methane selectivity at the end of the run with the unmodified catalyst relative to the silicon-modified catalyst was mostly caused by the 10% lower conversion with the unmodified catalyst After 500 hours operations were lined-out at 208° C. inlet temperature and 80% conversion. There was essentially no $C_2$ formation ($\leq 0.2\%$) with the subject silicon modified catalyst. The $C_3$ and $C_4$ selectivities were 1.3 and 1.9%, respectively, giving an overall $C_1$-$C_4$ selectivity no more than 4.8%. The $H_2:CO$ usage and feed ratios were equal since there was essentially no water gas shift activity.

Since the silicon-modified catalyst did not show any sign of further deactivation at 208° C. and 80% conversion after an initial activity loss during the first 20 hours at these conditions, the severity of operation was increased during further testing in order to determine the catalyst's stability. Between 825 and 933 hours the temperature and space velocity were increased in parallel from 210° C. to 224° C. and from 150 $hr^{-1}$, respectively, in order to maintain about 80% conversion. During the temperature increase period some deactivation occurred. Therefore, the space velocity increase was less than expected, based on an apparent activation energy of about 25 Kcal/mole. It is believed deactivation occurred possibly because a conversion level of 80% was too severe a condition at the high temperature. The catalyst deactivated to 70% conversion during the following 200 hours, after which it maintained constant conversion for the next 400 hours. The conversion decreased to 60% between 1542 and 1574 hours and showed no further activity loss until 1618 hours. Between 1618 and 1700 hours, which was the end of the run, there were operational problems which caused difficulties in interpreting the data. From the activity loss between 933 hours on stream to 1542 hours, a deactivation rate of about 0.016%/hour was calculated at 224° C..

There is not enough data presently available for calculating with certainty the expected commercial life of the silicon-modified ruthenium catalyst. Since there was no apparent deactivation at 208° C., half of the deactivation rate at 224° C. was roughly estimated to be an upper bound to the average deactivation rate between 208° C. and 224° C. A commercial run with beginning and end of run temperatures of 208° C. and 224° C., respectively, would then result in about 1 year catalyst life at 70-80% CO conversion, given an apparent activation energy of about 25 Kcal/mole. The catalyst would then have to be regenerated. Selectivities determined at 1050 hours are believed representative at end-of-run performance at 224° C.. They are 3.2% methane, less than 0.2% $C_2$, 2.1% $C_3$ and 2.9% $C_4$.

The invention accordingly can be characterized as a process for producing hydrocarbons from a feed stream comprising hydrogen and carbon oxides which comprises contacting the feed gas stream at conversion-promoting conditions with a solid catalyst and recovering a product stream comprising hydrocarbons having at least three carbon atoms per molecule, with the catalyst comprising (i) an inorganic oxide support, (ii) ruthenium particles having a particle size of about 40–60 Angstroms dispersed upon said support, and (iii) silicon in active contact with the ruthenium particles.

In order for the modifier component to have an effect on the electronic properties of atoms within the ruthenium particles, it is necessary for the modifier to be in active contact with the ruthenium. It is not believed necessary for the modifier element to form a compound with the ruthenium or to in any way form a bond with the ruthenium. It is believed sufficient for the modifier element atoms to be close enough that they may be considered as touching or in contact. The modifier element atoms can be located below the ruthenium particles if, for instance, the modifier is applied to the support prior to placement of the ruthenium particles on the support. The proper placement of the two components is best measured in terms of electronic interaction, as by the specified shift in electron energies described above, rather than by geometrical placement or measurement. Useful measurements can be determined using STEM (Scanning Transmission Electron Microscope) techniques.

Preferably the modifier component atoms are located on the sides, partially overlapping or upon the sides of the ruthenium particle. This result is more likely to occur if the ruthenium and modifier components are placed upon the support simultaneously as by reverse micelle techniques. Alternatively, the subject catalyst can be produced by adding the modifier component to the composite after the ruthenium component has been placed upon the support as by a normal impregnation in an aqueous solution of a salt of the modifier component. The ruthenium component is always placed upon the support using the micelle technique described above.

What is claimed is:

1. A process for producing $C_3$-plus hydrocarbons from carbon monoxide which comprises contracting a feed stream comprising hydrogen and carbon monoxide with a solid catalyst in a reaction zone maintained at conversion-promoting conditions and producing an effluent stream comprising $C_3$-plus hydrocarbons, with the catalyst comprising (i) an inorganic oxide support; (ii) about 0.3–6.0 wt. percent ruthenium present as particles of about 40–60 Angstroms and (iii) about 0.1–5 wt. % of a modifier component chosen from the group consisting of aluminum, silicon, lead, arsenic, and bismuth.

2. The process of claim 1, wherein the inorganic oxide is alumina.

3. The process of claim 1 wherein the inorganic oxide is titania.

4. A process for producing hydrocarbons from a feed stream comprising hydrogen and carbon monoxide which comprises contacting the feed gas stream at conversion-promoting-conditions with a solid catalyst and recovering a product stream comprising hydrocarbons having at least three carbon atoms per molecule, with the catalyst comprising (i) an inorganic oxide support, (ii) ruthenium particles having a particle size of about 40–60 Angstroms dispersed upon said support, and (iii) silicon in active contact with the ruthenium particles.

5. The process of claim 4 further characterized in that the catalyst comprises about 0.1 to 5 wt. percent silicon.

6. The process of claim 5 wherein the inorganic oxide support comprises alumina.

7. The process of claim 6 wherein the catalyst comprises about 0.3 to 6 wt. percent ruthenium.

8. The process of claim 5 wherein the inorganic oxide is titania.

9. A process for converting carbon monoxide to hydrocarbons which comprises passing a feed stream comprising a carbon monoxide and water and/or hydrogen into contact with a solid catalyst comprising an inorganic oxide support, a ruthenium component and about 0.1–5 wt. percent of a modifier component comprising silicon with the ruthenium component and the modifier component having been placed upon the support by simultaneous reverse micelle impregnation.

10. The process of claim 9 wherein the catalyst comprises about 0.3–6.0 wt. percent ruthenium.

11. The process of claim 10 wherein at least 80 wt. percent of the ruthenium present on the catalyst is present as particles of about 40 to 60 Angstroms.

12. The process of claim 9 wherein the catalyst comprises from 1.0 to 4.0 wt. percent ruthenium.

13. The process of claim 9 wherein the modifier component shifts the binding energy of the ruthenium component by 0.1 to 0.25 electron volts as measured by ESCA.

14. The process of claim 13 wherein the modifier component is 1 to 4.5 wt. percent silicon and the catalyst contains 1 to 4.0 wt. percent ruthenium.

* * * * *